United States Patent [19]

Kajiyashiki et al.

[11] Patent Number: 5,698,580
[45] Date of Patent: Dec. 16, 1997

[54] ANTIVIRAL AGENT CONTAINING BENZODITHIIN DERIVATIVE AS ACTIVE INGREDIENT

[75] Inventors: Tsuyoshi Kajiyashiki, Sagamihara; Ryu Sato, Morioka; Tomoyuki Yokota; Kenji Sudo, both of Fukushima; Wataru Watanabe, Takatsuki; Shiro Shigeta, Fukushima, all of Japan

[73] Assignee: Rational Drug Design Laboratories, Fukushima, Japan

[21] Appl. No.: 750,730

[22] PCT Filed: Jun. 6, 1995

[86] PCT No.: PCT/JP95/01107

§ 371 Date: Dec. 16, 1996

§ 102(e) Date: Dec. 16, 1996

[87] PCT Pub. No.: WO95/35292

PCT Pub. Date: Dec. 28, 1995

[30] Foreign Application Priority Data

Jun. 21, 1994 [JP] Japan .................. 6-138546

[51] Int. Cl.⁶ .................. A61K 31/385; C07D 339/08
[52] U.S. Cl. .................. 514/436; 549/20; 549/21
[58] Field of Search .................. 549/20, 21; 514/436

[56] References Cited

U.S. PATENT DOCUMENTS 3,682,953  8/1972  Sestanj .................. 260/327
3,845,047  10/1974 Egli et al. .................. 260/250

*Primary Examiner*—José G. Dees
*Assistant Examiner*—Mary C. Cebulak
*Attorney, Agent, or Firm*—Leydig, Voit & Mayer, Ltd.

[57] ABSTRACT

Antiviral agents comprising, as an active ingredient, a 1,4-dihydro-2,3-benzodithiin derivative of the formula

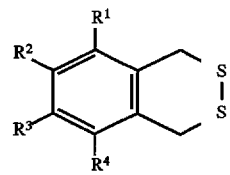

wherein each symbol is as defined in the Specification, or a pharmacologically acceptable salt thereof. The antiviral agents of the present invention have superior antiviral activity and are effective for the preventive and therapeutic treatment of viral diseases caused typically by RS virus.

3 Claims, No Drawings

ANTIVIRAL AGENT CONTAINING BENZODITHIIN DERIVATIVE AS ACTIVE INGREDIENT

This application is a 371 of PCT/JP95/01107 filed Jun. 6, 1995.

TECHNICAL FIELD

The present invention relates to an antiviral agent containing a 1,4-dihydro-2,3-benzodithiin derivative or a pharmacologically acceptable salt thereof as an active ingredient, and to a 1,4-dihydro-2,3-benzodithiin derivative which is the active ingredient of said antiviral agent. More particularly, the present invention relates to an antiviral agent efficacious for the preventive or therapeutic treatment of viral diseases represented by respiratory diseases such as oropharyngolaryngitis, inflammation of lower airway, bronchitis, bronchiolitis, croup and the like, which are caused by RS virus (Respiratory Syncytial virus).

BACKGROUND ART

As pharmaceutical agents useful for the therapy of viral diseases, there have been conventionally known anti-herpes agents [e.g. acyclovir (a guanine derivative), ganciclovir (a guanine derivative), idoxuridine (2'-deoxy-5-iodouridine) and vidarabine (an adenine derivative)], anti-influenza agents such as amantadine (1-amino-tricyclo[3.3.1.1$^{3,7}$]-decane), and the like. Meanwhile, Ribavirin which is a nucleic acid analog is used as an antiviral agent against RS virus which causes severe respiratory diseases in infants.

Yet, a pharmaceutical agent has not been developed, which exhibits sufficient therapeutic effects on viral diseases and which is associated with less toxicity and less side-effects. For example, Ribavirin, though effective against RS virus, has high toxicity and cannot be administered orally but only locally by inhalation. Ribavirin has been recognized to be teratogenic, carcinogenic and mutagenic, and is associated with difficulty in clinical application. Therefore, an antiviral agent has been desired, which shows clinically sufficient therapeutic effects and is associated with less toxicity and less side-effects.

It is therefore an object of the present invention to provide an antiviral agent having superior antiviral activity and less toxicity and less side-effects.

DISCLOSURE OF THE INVENTION

Accordingly, the present invention provides the following.

(1) Antiviral agents comprising, as an active ingredient, a 1,4-dihydro-2,3-benzodithiin derivative of the formula (I) [hereinafter sometimes referred to briefly as 1,4-dihydro-2,3-benzodithiin derivative (I)]

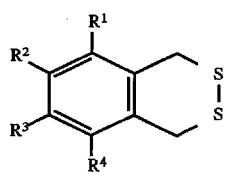

wherein $R^1$, $R^2$, $R^3$ and $R^4$ are each a hydrogen atom, an optionally substituted lower alkyl, an optionally substituted lower alkenyl, an optionally substituted aryl, an optionally substituted aralkyl, a nitro, a cyano, a carboxy, an alkoxycarbonyl, a lower alkylsulfinyl, an arylsulfinyl, a lower alkylsulfonyl, an arylsulfonyl, a sulfamoyl, a carbamoyl, an acyl, a hydrazino, a halogen atom, a group of the formula: $OR^5$, a group of the formula: $SR^5$ or a group of the formula: $NR^6R^7$ wherein $R^5$ is hydrogen atom, optionally substituted lower alkyl, optionally substituted lower alkenyl or optionally substituted aryl, and $R^6$ and $R^7$ are each hydrogen atom, optionally substituted lower alkyl, optionally substituted lower alkenyl or optionally substituted aryl, or a pharmacologically acceptable salt thereof.

(2) 1,4-Dihydro-2,3-benzodithiin derivatives of the formula (II)

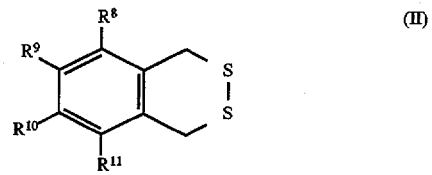

wherein $R^8$, $R^9$, $R^{10}$ and $R^{11}$ are each an optionally substituted lower alkyl or a halogen atom.

(3) Pharmaceutical compositions for therapy of viral diseases, which comprises, as an active ingredient, the 1,4-dihydro-2,3-benzodithiin derivative of the formula (I) of (1) or a pharmacologically acceptable salt thereof.

(4) Methods for treating viral dishes, which comprise administering to patients a pharmaceutically effective amount of the 1,4-dihydro-2,3-benzodithiin derivative of the formula (I) of (1) or a pharmacologically acceptable salt thereof.

(5) Use of the 1,4-dihydro-2,3-benzodithiin derivative of the formula (I) of (1) or a pharmacologically acceptable salt thereof for the therapy of viral diseases.

(6) Use of the 1,4-dihydro-2,3-benzodithiin derivative of the formula (I) of (1) or a pharmacologically acceptable salt thereof for the production of a pharmaceutical composition for the therapy of viral diseases.

In the above-mentioned formulas (I) and (II), each symbol denotes the following.

The lower alkyl at $R^1$, $R^2$, $R^3$, $R^4$, $R^5$, $R^6$, $R^7$, $R^8$, $R^9$, $R^{10}$ and $R^{11}$, which is an optionally substituted lower aryl, may be a linear or branched one. Examples thereof include methyl, ethyl, propyl, isopropyl, butyl, isobutyl, t-butyl, pentyl and the like. These groups may have substituent(s) such as optionally substituted cycloalkyl; optionally substituted heterocycle; lower alkylamino (e.g., methylamino, dimethylamino, isopropylamino and t-butylamino); lower alkoxy (e.g., method, isopropoxy and t-butoxy); hydroxy; carboxy; alkoxycarbonyl (e.g., methoxycarbonyl, propoxycarbonyl and t-butoxycarbonyl); and cyano.

The cycloalkyl of optionally substituted cycloalkyl is exemplified by cyclohexyl, cyclopentyl and the like. These groups may have, as substituent(s), lower alkyl such as methyl, isopropyl and pentyl; hydroxy; lower alkoxy such as methoxy, isopropoxy and t-butoxy; halogen atom such as fluorine atom, chlorine atom and bromine atom; lower alkylamino such as methylamino, dimethylamino, isopropylamino and t-butylamino; lower alkylthio such as methylthio, ethylthio, isopropylthio and neopentylthio; arylthio such as phenylthio, tolylthio and 1-naphthylthio; acyl such as acetyl, propionyl and t-butoxy; lower alkylcarbonyloxy such as acetyloxy, isopropionyloxy and t-butyryloxy; and the like. Examples of heterocyclic group of the optionally substituted heterocyclic group include pyridyl, pyrazyl, quinolyl, thienyl, tetrazolyl, furanyl, pyrrolidyl, piperazyl, morpholyl and the like. These groups may have, as substituent(s), the groups recited for the definition of the above-mentioned optionally substituted cycloalkyl.

The lower alkenyl at $R^1$, $R^2$, $R^3$, $R^4$, $R^5$, $R^6$ and $R^7$, which is an optionally substituted lower alkenyl, may be a linear or branched one. Examples thereof include vinyl, propenyl, isopropenyl, prenyl and the like. These groups may have, as substituent(s), the groups recited for the definition of the above-mentioned optionally substituted lower alkyl.

The aryl at $R^1$, $R^2$, $R^3$, $R^4$, $R^5$, $R^6$ and $R^7$, which is an optionally substituted aryl, is exemplified by phenyl, naphthyl and the like. These groups may have, as substituent(s), the groups recited for the definition of the above-mentioned optionally substituted cycloalkyl.

The aralkyl at $R^1$, $R^2$, $R^3$ and $R^4$, which is an optionally substituted aralkyl, is exemplified by benzyl, phenethyl, phenylpropyl, naphthylethyl and the like. These groups may have, as substituent(s), the groups recited for the definition of the above-mentioned optionally substituted cycloalkyl.

The alkoxycarbonyl at $R^1$, $R^2$, $R^3$ and $R^4$ is exemplified by methoxycarbonyl, ethoxycarbonyl, isopropoxycarbonyl, t-butoxycarbonyl and the like.

The lower alkylsulfinyl at $R^1$, $R^2$, $R^3$ and $R^4$ is exemplified by methylsulfinyl, isopropylsulfinyl and the like.

The arylsulfinyl at $R^1$, $R^2$, $R^3$ and $R^4$ is exemplified by phenylsulfinyl, p-methoxyphenylsulfinyl and the like.

The lower alkylsulfonyl at $R^1$, $R^2$, $R^3$ and $R^4$ is exemplified by methylsulfonyl, isopropylsulfonyl and the like.

The arylsulfonyl at $R^1$, $R^2$, $R^3$ and $R^4$ is exemplified by phenylsulfonyl, p-methoxyphenylsulfonyl and the like.

The acyl at $R^1$, $R^2$, $R^3$ and $R^4$ is exemplified by acetyl, propionyl, isobutyryl, pivaloyl and the like.

The halogen atom at $R^1$, $R^2$, $R^3$, $R^4$, $R^8$, $R^9$, $R^{10}$ and $R^{11}$ is exemplified by fluorine atom, chlorine atom, bromine atom and the like.

The salts of 1,4-dihydro-2,3-benzodithiin derivative (I) include, for example, acid addition salts with inorganic acid such as hydrochloric acid, sulfuric acid, hydrobromic acid and phosphoric acid, and acid addition salts with organic acid such as fumaric acid, tartaric acid, succinic acid, citric acid and methanesulfonic acid.

The typical 1,4-dihydro-2,3-benzodithiin derivatives (I) are as follows.

(1) 1,4-dihydro-2,3-benzodithiin (Compound 1)

(2) 1,4-dihydro-6-nitro-2,3-benzodithiin (Compound 2)

(3) 6-amino-1,4-dihydro-2,3-benzodithiin (Compound 3)

(4) methyl 1,4-dihydro-2,3-benzodithiin-6-carboxylate (Compound 4)

(5) 1,4-dihydro-2,3-benzodithiin-6-carboxylic acid (Compound 5)

(6) 1,4-dihydro-6-methyl-2,3-benzodithiin (Compound 6)

(7) 6-benzyloxy-1,4-dihydro-2,3-benzodithiin (Compound 7)

(8) 1,4-dihydro-6-methoxy-2,3-benzodithiin (Compound 8)

(9) 1,4-dihydro-6-fluoro-2,3-benzodithiin (Compound 9)

(10) 1,4-dihydro-5-fluoro-2,3-benzodithiin (Compound 10)

(11) 6-chloro-1,4-dihydro-2,3-benzodithiin (Compound 11)

(12) 1,4-dihydro-6-N,N-dimethylamino-2,3-benzodithiin (Compound 12)

(13) 6-tert-butyl-1,4-dihydro-2,3-benzodithiin (Compound 13)

The 1,4-dihydro-2,3-benzodithiin derivative (I) can be produced, for example, by the following reaction steps.

Reaction Steps

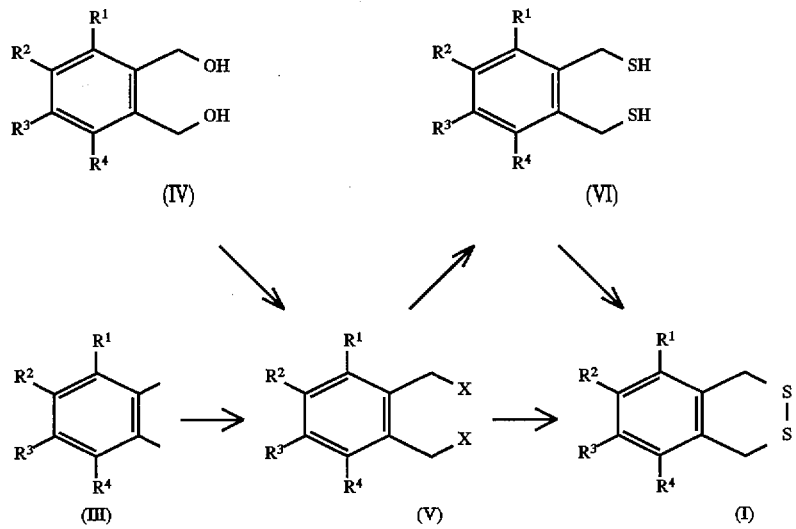

In the above reaction steps, $R^1$, $R^2$, $R^3$ and $R^4$ are as defined above and X is a halogen atom. The halogen atom at X is exemplified by fluorine atom, chlorine atom, bromine atom and the like.

The above reaction steps are explained in the following.

A dimethylbenzene derivative of the formula (III) is reacted with a halogenating agent such as N-halogenosuccinimide in the coexistence of a catalytic amount of benzoyl peroxide or light to give a dihalogenomethylbenzene derivative of the formula (V). The dihalogenomethylbenzene derivative of the formula (V) can be also obtained by reacting a dihydroxymethylbenzene derivative of the formula (IV) with a halogenating agent such as phosphorus tribromide.

The obtained dihalogenomethylbenzene derivative of the formula (V) is reacted with potassium thioacetate to give a dithioacetylbenzene derivative, or a bisisothiouronium salt obtained by reacting the dihalogenomethylbenezene derivative of the formula (V) with thiourea is reacted with a base such as sodium hydroxide to give a dimercaptomethylbenzene derivative of the formula (VI). Then, the obtained dimercaptomethylbenzene derivative of the formula (VI) is reacted with an oxidizing agent such as hydrogen peroxide to give a 1,4-dihydro-2,3-benzodithiin derivative (I).

The 1,4-dihydro-2,3-benzodithiin derivative (I) can be also obtained by reacting the dihalogenomethylbenezene derivative of the formula (V) with bis (benzyltriethylammonium) tetrathiomolybdate.

The 1,4-dihydro-2,3-benzodithiin derivative (I) thus obtained can be isolated and purified from a reaction mixture by a method similar to the one generally used for isolating and purifying an organic compound from a reaction mixture. For example, the reaction mixture is poured into water; the mixture is extracted with an organic solvent such as diethyl ether and ethyl acetate; the extract is washed successively with cold dilute hydrochloric acid, aqueous sodium hydrogencarbonate solution, brine and the like; after drying, the residue is concentrated to give a crude product; and the crude product is purified as necessary by recrystallization, chromatography and the like to give a 1,4-dihydro-2,3-benzodithiin derivative (I).

The salt of 1,4-dihydro-2,3-benzodithiin derivative (I) can be produced by conventional salt forming reactions.

The dimethylbenzene derivative of the formula (III) to be the starting material can be produced by the method described in Journal of American Chemical Society, vol. 70, pp. 2218–2219 (1948) or ibid., vol. 72, pp. 4809–4810 (1950). The dihydroxymethylbenzene derivative of the formula (IV) can be produced by the method described in Synthetic Communications, vol. 21, 8–9 combined volume, pp. 1055–1069 (1991) or the method described in Japanese Patent Unexamined Publication No. 45126/1982.

The 1,4-dihydro-2,3-benzodithiin derivative (I) and salts thereof have useful pharmacological properties, particularly antiviral activity, and are useful for preventive and therapeutic treatment of human and other mammals such as cow, horse, mouse, rat, rabbit, dog and cat infected with a virus or at the risk of being infected with viruses. Examples of such viruses include DNA type viruses such as herpes simplex virus type 1, herpes simplex virus type 2, human cytomegalovirus, Epstein-Barr virus, Varicella Zoster virus and human herpes virus type 6 belonging to the family Herpesviridae; human adenovirus belonging to the family Adenoviridae; hepatitis B virus belonging to the family Hepadnaviridae; human papilloma virus belonging to the family Papovaviridae; and the like.

As the RNA type viruses, exemplified are rubella virus, Japanese encephalitis virus and hepatitis C virus belonging to the family Togaviridae; measles virus, parainfluenza virus, respiratory syncytial virus and mumps virus belonging to the family Paramyxoviridae; influenza virus belonging to the family Orthomyxoviridae; human immunodeficiency virus and human T-lymphotropic virus belonging to the family Retroviridae; rabies virus belonging to the family Rhabdoviridae; human polio virus and hepatitis A virus belonging to the family Picornaviridae; Ebola virus and Marburg virus belonging to the family Filoviridae; and the like.

The anti-RS viral activity of 1,4-dihydro-2,3-benzodithiin derivative (I) and salts thereof is evident from the experimental examples to be mentioned later. In addition, it has been confirmed that 1,4-dihydro-2,3-benzodithiin derivative (I) and salts thereof are low toxic and cause less side-effects.

While the dose of 1,4-dihydro-2,3-benzodithiin derivative (I) and salts thereof varies depending on diseases, severity of the conditions of patients, tolerance to drugs and the like, it is generally 10–1,000 mg, preferably 100–500 mg, daily for an adult, which is administered in a single dose or several doses. They can be formulated into an optional dosage form suitable for the administration mute.

The 1,4-dihydro-2,3-benzodithiin derivative (I) and salts thereof can be optionally prepared into a suitable form for administration by a conventional formulation method. Thus, the antiviral agent of the present invention encompasses pharmaceutical compositions for treatment containing 1,4-dihydro-2,3-benzodithiin derivative (I) or a salt thereof. Such compositions can be prepared by a conventional method optionally using desired pharmaceutical carriers, pharmaceutically acceptable additives such as excipients, and the like.

When this composition is an oral preparation, it is desirably prepared into a form suitable for absorption from the digestive tract. The oral tablets and capsules are unit administration dose forms, and may contain binders such as syrup, gum arabic, gelatin, sorbitol, tragacanth and polyvinylpyrrolidone; excipients such as lactose, corn starch, calcium phosphate, sorbitol and glycine; lubricants such as magnesium stearate, talc, polyethylene glycol and silica; disintegrants such as potato starch; acceptable wetting agents such as sodium lauryl sulfate; and the like. The tablets may be coated by a method known in this field. Liquid oral preparation may be aqueous or oily suspension, solution, syrup, elixir and the like. Such liquid preparation may contain conventional additives such as suspending agents (e.g., sorbitol syrup, methylcellulose, glucose/sugar syrup, gelatin, hydroxyethylcellulose, carboxymethylcellulose, aluminum stearate gel and hydrogenated edible fat); emulsifiers such as lecithin, sorbitan monooleate and gum arabic; nonaqueous vehicles such as almond oil, fractionated coconut oil, oily ester, propylene glycol and ethanol; preservatives such as methyl p-hydroxybenzoate, propyl p-hydroxybenzoate and sorbic acid; and the like. Oral preparation may be a solid preparation to be dissolved in water or other suitable vehicle before use.

When this composition is an injection, pH adjusting agents, buffers, stabilizers, preservatives, solubilizers and the like are added as necessary to the 1,4-dihydro-2,3-benzodithiin derivative (I) or a salt thereof and the mixture is prepared into a subcutaneous, intramuscular or intravenous injection by a conventional method. When this composition is an aerosol, for example, propellants such as chlorofluorohydrocarbon can be added.

EXAMPLES

The present invention is explained in more detail by illustrative Examples to which the present invention is not limited.

Production Example 1

Synthesis of o-xylene-α,α'-dithiole

α,α'-Dibromo-o-xylene (6.6 g, 25.0 mmol) was dissolved in ethanol (130 ml) under a nitrogen atmosphere, and thiourea (4.8 g, 63.0 mmol) was added, which was followed by reflux under heating for 9 hours. The reaction mixture was cooled to room temperature and the solvent was evaporated under reduced pressure. Water (100 ml) and 3.3M aqueous sodium hydroxide solution (30 ml) were successively added, and the mixture was refluxed under heating for 5 hours under a nitrogen atmosphere. The reaction mixture was cooled to room temperature and conc. sulfuric acid was added until it assumed acidity. The mixture was extracted with methylene chloride and the organic extract was dried over anhydrous sodium sulfate. The residue obtained by subsequent filtration and concentration was recrystallized from hexane to give 2.7 g of o-xylene-α,α'-dithiole as white crystals (yield 64%).

Production Example 2

Synthesis of 1,4-Dihydro-2,3-benzodithiin (Compound 1)

o-Xylene-α,α'-dithiole (1.7 g, 10.0 mmol) obtained in Production Example 1 was dissolved in a mixed solvent of acetic acid (50 ml) and methanol (50 ml). To this solution was dropwise added a solution of iron(II) chloride 6 hydrate (8.1 g, 30.0 mmol) in acetic acid (25 ml) at 60° C., and the mixture was stirred with heating for one hour at the same temperature. Water was added to the reaction mixture and the mixture was extracted with methylene chloride. After washing the organic extract with 5% aqueous sodium hydrogencarbonate solution until it was neutralized, the mixture was dried over anhydrous sodium sulfate. The residue obtained by subsequent filtration and concentration was recrystallized from hexane to give 907 mg of 1,4-dihydro-2,3-benzodithiin (Compound 1) having the following properties as white crystals (yield 54%).

m.p. 77°–78° C., NMR spectrum (270 MHz, CDCl$_3$, trimethylsilane) δ (ppm), 7.30–6.98 (m, 4H), 4.07 (s, 4H).

Production Example 3

Synthesis of 1,2-Bibromomethyl-4-nitrobenzene 1,2-Dimethyl-4-nitrobenzene (151 g, 1.0 mol) was dissolved in carbon tetrachloride (1 l), and N-bromosuccinimide (356 g, 1.0 mol) and benzoyl peroxide (5 g, 16.7 mmol) were added at room temperature, which was followed by reflux under heating for 2.5 hours. The reaction mixture was cooled to room temperature and the precipitated crystals were collected by filtration. The solvent was evaporated under reduced pressure and the obtained residue was recrystallized from ethanol to give 96 g of 1,2-dibromomethyl-4-nitrobenzene (yield 29%).

Production Example 4

Synthesis of Bis(benzyltriethylammonium) Tetrathiomolybdate

To a suspension of thiomolybdic acid (50.9 g, 196 mmol) in water (80 ml) was dropwise added at room temperature a solution of benzyltriethylammonium chloride (91.2 g, 400 mmol) in water (190 ml), and the mixture was stirred at room temperature for 2 hours. The precipitated crystals were collected by filtration, and washed successively with isopropyl alcohol and diethyl ether and dried in vacuo in the presence of phosphorus pentaoxide to give 104 g of bis(benzyltriethylammonium) tetrathiomolybdate (yield 87%).

Production Example 5

Synthesis of 1,4-Dihydro-6-nitro-2,3-benzodithiin (Compound 2)

Bis(benzyltriethylammonium) tetrathiomolybdate (18.4 g, 30.2 mmol) obtained in Production Example 4 was dissolved in chloroform (120 ml), and a solution of 1,2-dibromomethyl-4-nitrobenzene (4.24 g, 13.7 mmol) obtained in Production Example 3 in chloroform (120 ml) was dropwise added at room temperature, which was followed by stirring at room temperature for 2 hours. The reaction mixture was filtered and the solvent was evaporated under reduced pressure. Separation and purification by silica gel column chromatography [developing solution: a mixed solution of chloroform and hexane (volume ratio 2:1)] gave 900 mg of 1,4-dihydro-6-nitro-2,3-benzodithiin (Compound 2) having the following properties (yield 31%).

Mass spectrum [M]$^+$: 213, NMR spectrum (270 MHz, CDCl$_3$, trimethylsilane) δ (ppm), 8.12–7.38 (m, 4H), 4.28 (s, 4H).

Production Example 6

Synthesis of 6-Amino-1,4-dihydro-2,3-benzodithiin (Compound 3)

1,4-Dihydro-6-nitro-2,3-benzodithiin (340 mg, 1.59 mmol) obtained in Production Example 5 was dissolved in methanol (50 ml), and 5% aqueous ammonia (12 ml) and sodium hydrosulfite (2.79 g, 16.0 mmol) were added, which was followed by stirring at room temperature for 10 minutes. Water was added to the reaction mixture, and the mixture was extracted with ethyl acetate. The organic extract was washed with saturated brine, dried over anhydrous sodium sulfate, filtered and concentrated. The obtained residue was separated and purified by silica gel column chromatography (developing solution: chloroform) to give 33.7 mg of 6-amino-1,4-dihydro-2,3-benzodithiin (Compound 3) having the following properties (yield 9.9%).

Mass spectrum [M]$^+$: 183, NMR spectrum (270 MHz, CDCl$_3$, trimethylsilane) δ (ppm), 6.83–6.41 (m, 4H), 3.85 (s, 4H), 3.47 (brd, 2H).

Production Example 7

Synthesis of Methyl 3,4-Dimethylbenzoate 3,4-Dimethylbenzoic acid (64.4 g, 429 mmol) was dissolved in methanol (600 ml), and sulfuric acid (9 ml) was added, which was followed by reflux under heating for 5 hours. The reaction mixture was concentrated to 160 ml and water was added. The mixture was extracted with ethyl acetate, and the organic extract was washed successively with water, 10% aqueous sodium hydroxide solution and saturated brine, dried over anhydrous sodium sulfate, filtered and concentrated to give 68.0 g of methyl 3,4-dimethylbenzoate (yield 97%).

Production Example 8

Synthesis of Methyl 3,4-Dibromomethylbenzoate

In the same manner as in Production Example 3 except that methyl 3,4-dimethylbenzoate obtained in Production Example 7 was used instead of 1,2-dimethyl-4-nitrobenzene, reaction, separation and purification were carried out to give methyl 3,4-dibromomethylbenzoate.

Production Example 9

Synthesis of 3,4-Dibromomethylbenzoic Acid

Methyl 3,4-dibromomethylbenzoate (10.0 g, 31.1 mmol) obtained in Production Example 8 was dissolved in acetic acid (100 ml), and 47% hydrobromic acid (100 ml) was added, which was followed by reflux under heating for 3.5 hours. The reaction mixture was cooled to room temperature and poured into ice-water. The precipitated crystals were collected by filtration. The obtained crystals were dissolved in ethyl acetate and dried over anhydrous sodium sulfate. The solvent was evaporated under reduced pressure to give 8.12 g of 3,4-dibromomethylbenzoic acid (yield 81%).

Production Examples 10 and 11

Syntheses of Methyl 1,4-Dihydro-2,3-benzodithiin-6-carboxylate (Compound 4) and 1,4-Dihydro-2,3-benzodithiin-6-carboxylic Acid (Compound 5)

In the same manner as in Production Example 5 except that, instead of 1,2-dibromomethyl-4-nitrobenzene, methyl 3,4-dibromomethylbenzoate obtained in Production Example 8 was used (Production Example 10) and 3,4-dibromomethylbenzoic acid obtained in Production Example 9 was used (Production Example 11), reaction, separation and purification were carried out to give the corresponding methyl 1,4-dihydro-2,3-benzodithiin-6-carboxylate (Compound 4) and 1,4-dihydro-2,3-benzodithiin-6-carboxylic acid (Compound 5), respectively.

The properties of Compound 4 were as follows.

Mass spectrum $[M]^+$: 226, NMR spectrum (270 MHz, $CDCl_3$, trimethylsilane) δ (ppm), 7.86–7.06 (m, 4H), 4.08 (s, 4H), 3.90 (s, 3H).

The properties of Compound 5 were as follows.

Mass spectrum $[M]^+$: 212, NMR spectrum (270 MHz, $CDCl_3$, trimethylsilane) δ (ppm), 13.00 (s, 1H), 7.82–7.25 (m, 4H), 4.22 (s, 4H).

Production Example 12

Synthesis of 3,4-Dihydroxymethyltoluene

4-Methylphthalic acid (1.40 g, 7.8 mmol) was dissolved in tetrahydrofuran (80 ml) under an argon atmosphere, and lithium aluminum hydride (742 mg, 19.5 mmol) was added, which was followed by reflux under heating for 4 hours. Water was added to the reaction mixture on an ice bath, and the mixture was extracted with ethyl acetate. The organic extract was washed successively with saturated aqueous potassium sodium tartrate solution, water and saturated brine, dried over anhydrous sodium sulfate, filtered and concentrated. The obtained residue was separated and purified by silica gel column chromatography [developing solution: a mixed solution of ethyl acetate and hexane (volume ratio 2:3)] to give 759 mg of 3,4-dihydroxymethyltoluene (yield 64%).

Production Example 13

Synthesis of 3,4-Dibromomethyltoluene 3,4-Dihydroxymethyltoluene (579 mg, 4.99 mmol) obtained in Production Example 12 was dissolved in benzene (5 ml), and phosphorus tribromide (276 ml, 2.91 mmol) was added, which was followed by stirring at room temperature for 4 hours. The reaction mixture was poured into ice-water, and the mixture was extracted with methylene chloride. The organic extract was washed successively with saturated aqueous sodium hydrogencarbonate solution and saturated brine, filtered and concentrated. The obtained residue was separated and purified by silica gel column chromatography [developing solution: a mixed solution of ethyl acetate and hexane (volume ratio 1:3)] to give 1.11 g of 3,4-dibromomethyltoluene (yield 80%).

Production Example 14

Synthesis of 1,4-Dihydro-6-methyl-2,3-benzodithiin (Compound 6)

In the same manner as in Production Example 5 except that 3,4-dibromomethyltoluene obtained in Production Example 13 was used instead of 1,2-dibromomethyl-4-nitrobenzene, reaction, separation and purification were carried out to give 1,4-dihydro-6-methyl-2,3-benzodithiin (Compound 6) having the following property.

NMR spectrum (270 MHz, $CDCl_3$, trimethylsilane) δ (ppm), 6.98 (s, 2H), 6.90 (s, 1H), 4.02 (s, 4H), 2.30 (s, 3H).

Production Example 15

Synthesis of 6-Benzyloxy-1,4-dihydro-2,3-benzodithiin (Compound 7)

In the same manner as in Production Example 12 except that 4-benzyloxyphthalic acid was used instead of 4-methylphthalic acid, reaction, separation and purification were carried out to give 1-benzyloxy-3,4-dihydroxymethylbenzene. Then, in the same manner as in Production Example 13 except that 1-benzyloxy-3,4-dihydroxymethylbenzene was used instead of 3,4-dihydroxymethyltoluene, reaction, separation and purification were carried out to give 1-benzyloxy-3,4-dibromomethylbenzene. Then, in the same manner as in Production Example 5 except that 1-benzyloxy-3,4-dibromomethylbenzene was used instead of 1,2-dibromomethyl-4-nitrobenzene, reaction, separation and purification were carried out to give 6-benzyloxy-1,4-dihydro-2,3-benzodithiin (Compound 7) having the following property.

NMR spectrum (270 MHz, $CDCl_3$, trimethylsilane) δ (ppm), 7.30 (m, 5H), 6.99–6.71 (m, 3H), 5.04 (s, 2H), 4.02 (s, 2H), 4.01 (s, 2H).

Production Example 16

Synthesis of 1,4-Dihydro-6-methoxy-2,3-benzodithiin (Compound 8)

In the same manner as in Production Example 3 except that 1,2-dimethyl-4-methoxybenzene was used instead of 1,2-dimethyl-4-nitrobenzene, reaction, separation and purification were carried out to give 1,2-dibromomethyl-4-methoxybenzene. Then, in the same manner as in Production Example 5 except that 1,2-dibromomethyl-4-methoxybenzene was used instead of 1,2-dibromomethyl-4-nitrobenzene, reaction, separation and purification were carried out to give 1,4-dihydro-6-methoxy-2,3-benzodithiin (Compound 8) having the following property.

NMR spectrum (270 MHz, $CDCl_3$, trimethylsilane) δ (ppm), 7.00–6.62 (m, 4H), 4.03 (s, 2H), 4.01 (s, 2H), 3.78 (s, 3H).

Production Example 17

Synthesis of 1,4-Dihydro-6-fluoro-2,3-benzodithiin (Compound 9)

In the same manner as in Production Example 3 except that 1,2-dimethyl-4-fluorobenzene was used instead of 1,2-dimethyl-4 -nitrobenzene, reaction, separation and purification were carried out to give 1,2-dibromomethyl-4-fluorobenzene. Then, in the same manner as in Production Example 5 except that 1,2-dibromomethyl-4-fluorobenzene was used instead of 1,2-dibromomethyl-4-nitrobenzene, reaction, separation and purification were carried out to give 1,4-dihydro-6-fluoro-2,3-benzodithiin (Compound 9) having the following property.

NMR spectrum (270 MHz, $CDCl_3$, trimethylsilane) δ (ppm), 7.05–6.81 (m, 3H), 4.03 (s, 4H).

Production Example 18

Synthesis of 1,4-Dihydro-5-fluoro-2,3-benzodithiin (Compound 10)

In the same manner as in Production Example 3 except that 1,2-dimethyl-3-fluorobenzene was used instead of 1,2-dimethyl-4-nitrobenzene, reaction, separation and purification were carried out to give 1,2-dibromomethyl-3-fluorobenzene. Then, in the same manner as in Production Example 5 except that 1,2-dibromomethyl-3-fluorobenzene was used instead of 1,2-dibromomethyl-4-nitrobenzene, reaction, separation and purification were carried out to give 1,4-dihydro-5-fluoro-2,3-benzodithiin (Compound 10) having the following property.

NMR spectrum (270 MHz, $CDCl_3$, trimethylsilane) $\delta$ (ppm), 7.17–6.88 (m, 3H), 4.06 (s, 2H), 4.02 (s, 2H).

Production Example 19

Synthesis of 6-Chloro-1,4-dihydro-2,3-benzodithiin (Compound 11)

In the same manner as in Production Example 3 except that 4-chloro-1,2-dimethylbenzene was used instead of 1,2-dimethyl-4-nitrobenzene, reaction, separation and purification were carried out to give 4-chloro-1,2-dibromomethylbenzene. Then, in the same manner as in Production Example 5 except that 4-chloro-1,2-dibromomethylbenzene was used instead of 1,2-dibromomethyl-4-nitrobenzene, reaction, separation and purification were carried out to give 6-chloro-1,4-dihydro-2,3-benzodithiin (Compound 11) having the following property.

NMR spectrum (270 MHz, $CDCl_3$, trimethylsilane) $\delta$ (ppm), 7.15–7.02 (m, 3H), 4.02 (s, 4H).

Production Example 20

Synthesis of Dimethyl 4-N,N-dimethylaminophthalate

Dimethyl 4-nitrophthalate (24.5 g, 102 mmol) was dissolved in methanol (350 ml), and 35% formalin (40 ml) and palladium-carbon (5 g, containing palladium by 5%) were added. The mixture was stirred at room temperature for 9 hours under a hydrogen atmosphere until hydrogen absorption ended. The catalyst was removed and the mixture was concentrated to give 28 g of dimethyl 4-N,N-dimethylaminophthalate as a crude product.

Production Example 21

Synthesis of 1,4-Dihydro-6-N,N-dimethylamino-2,3-benzodithiin (Compound 12)

In the same manner as in Production Example 12 except that dimethyl 4-N,N-dimethylaminophthalate was used instead of 4-methylphthalic acid, reaction, separation and purification were carried out to give 3,4-dihydroxymethyl-N,N-dimethylaminobenzene. Then, in the same manner as in Production Example 13 except that 3,4-dihydroxymethyl-N,N-dimethylaminobenzene was used instead of 3,4-dihydroxymethyltoluene, reaction, separation and purification were carried out to give 3,4-dibromomethyl-N,N-dimethylaminobenzene. Then, in the same manner as in Production Example 5 except that 3,4-dibromomethyl-N,N-dimethylaminobenzene was used instead of 1,2-dibromomethyl-4-nitrobenzene, reaction, separation and purification were carried out to give 1,4-dihydro-6-N,N-dimethylamino-2,3-benzodithiin (Compound 12) having the following property.

NMR spectrum (270 MHz, $CDCl_3$, trimethylsilane) $\delta$ (ppm), 7.01–6.38 (m, 3H), 3.99 (s, 4H), 2.90 (s, 6H).

Production Example 22

Synthesis of 6-tert-Butyl-1,4-dihydro-2,3-benzodithiin (Compound 13)

In the same manner as in Production Example 3 except that 4-tert-butyl-1,2-dimethylbenzene was used instead of 1,2-dimethyl-4-nitrobenzene, reaction, separation and purification were carried out to give 1-tert-butyl-3,4-dibromomethylbenzene. Then, in the same manner as in Production Example 5 except that 1-tert-butyl-3,4-dibromomethylbenzene was used instead of 1,2-dibromomethyl-4-nitrobenzene, reaction, separation and purification were carried out to give 6-tert-butyl-1,4-dihydro-2,3-benzodithiin (Compound 13).

Formulation Examples are given in the following.

Formulation Example 1

Capsule

| | |
|---|---|
| Compound 1 | 20 g |
| Crystalline cellulose | 65 g |
| Corn starch | 20 g |
| Lactose | 22 g |
| Polyvinylpyrrolidone | 3 g |
| Total | 130 g |

The above ingredients were granulated by a conventional method and packed in 1000 capsules of gelatin hard capsule, each capsule containing 20 mg of Compound 1.

Formulation Example 2

Powder

| | |
|---|---|
| Compound 1 | 50 g |
| Crystalline cellulose | 400 g |
| Corn starch | 550 g |
| Total | 1000 g |

Compound 1 was dissolved in acetone, and the obtained solution was adsorbed on crystalline cellulose and dried. The dried cellulose was admixed with corn starch and prepared into a 20-fold powder of Compound 1 by a conventional method.

Formulation Example 3

Tablet

| | |
|---|---|
| Compound 1 | 10 g |
| Crystalline cellulose | 35 g |
| Corn starch | 10 g |
| Lactose | 20 g |
| Carboxymethylcellulose calcium | 10 g |
| Polyvinylpyrrolidone | 5 g |

| | |
|---|---|
| Talc | 10 g |
| Total | 100 g |

Compound 1 was dissolved in acetone, and the obtained solution was adsorbed on crystalline cellulose and dried. The dried cellulose was admixed with corn starch, lactose and carboxymethylcellulose calcium, and an aqueous solution of polyvinylpyrrolidone was added as a binder, which was followed by admixing and compression into tablets (100 mg per tablet). Each tablet contained 10 mg of Compound 1.

Experimental Examples are shown in the following.

Experimental Example 1

Suppression of RS Virus Assayed by the MTT Method

Maintenance media (Eagle's MEM media supplemented with 2% bovine serum albumin) containing compounds 1–13 or Ribavirin (control drug) at various concentrations, a HeLa cell suspension prepared in advance by digestion with trypsin, and maintenance media containing RS virus Long strain were plated in 96 well round-bottom microplates, and centrifuged at a low speed (700×g) for 5 minutes at room temperature. After the completion of the centrifugation, the media were incubated in a $CO_2$ gas incubator at 35° C. for 5 days. The MTT [3-(4,5-dimethylthiazol-2-yl)-2,5-diphenyltetrazolium bromide] solution was added to the media at 4 hours before the completion of the incubation, and the proportion of viable cells was colorimetrically determined on a microplate reader. The concentration of the compound at which cell destruction by RS virus infection was inhibited by 50% is shown as antiviral activity ($EC_{50}$). In addition, 50% cytotoxicity value ($CC_{50}$) of the compound was calculated from the tests run concurrently without inoculation of RS virus. The ratio of $CC_{50}$ to $EC_{50}$ was determined as S.I. (selectivity index, $CC_{50}/EC_{50}$). The results are shown in Table 1.

TABLE 1

| Test drug | $EC_{50}$ (μg/ml) | $CC_{50}$ (μg/ml) | S.I. |
|---|---|---|---|
| Compound 1 | 0.3 | 43.0 | 143.3 |
| Compound 2 | 1.9 | 8.9 | 4.7 |
| Compound 3 | 3.0 | 5.1 | 1.7 |
| Compound 4 | 1.8 | 9.7 | 5.4 |
| Compound 5 | 11.8 | 47.2 | 4.0 |
| Compound 6 | 0.2 | 44.7 | 224 |
| Compound 7 | >9.6 | 9.6 | — |
| Compound 8 | 1.6 | 12.8 | 8.0 |
| Compound 9 | 0.8 | 57.7 | 72.1 |
| Compound 10 | 1.1 | >100 | >90.9 |
| Compound 11 | 1.7 | 16.8 | 9.9 |
| Compound 12 | 2.3 | 33.3 | 14.5 |
| Compound 13 | 6.5 | 15.2 | 2.3 |
| Ribavirin | 7.6 | >100 | 13.2 |

Experimental Example 2

Suppression of RS Virus Assayed by Plaque Reduction Method

The confluently grown HeLa cells in 24 well flat-bottom multitrays were inoculated with RS virus Long strain prepared in a maintenance medium (Eagle's MEM medium supplemented with 2% bovine serum albumin), and the cells were incubated in a $CO_2$ gas incubator at 35° C. for one hour. Culture solution was discarded and the cells were washed with a maintenance medium. Then, maintenance media (supplemented with 0.6% methylcellulose) containing Compound 1 or Ribavirin (control drug) at various concentrations were added, and the media were incubated in a $CO_2$ gas incubator at 35° C. for 4 days. After the completion of the incubation, the cells were fixed with a 5% aqueous formalin solution for 6 hours and washed with tap water. Then, the cells were stained with a 0.025% aqueous crystal violet solution. The infected cell plaques which were not stained with crystal violet were microscopically counted. The plaques formed using the compound at various concentrations and those of control group without the compound were counted, and the concentration of the compound at which the number of plaques was decreased by 50% is shown as an antiviral activity ($EC_{50}$). In addition, 50% cytotoxicity ($CC_{50}$) of the compound was calculated by the MTT method. The ratio of $CC_{50}$ to $EC_{50}$ was determined as S.I. (selectivity index, $CC_{50}/EC_{50}$). The results are shown in Table 2.

TABLE 2

| | $EC_{50}$ (μg/ml) | $CC_{50}$ (μg/ml) | S.I. |
|---|---|---|---|
| Compound 1 | 1.7 | 44.7 | 26.29 |
| Ribavirin | 3.7 | >100 | 27.03 |

As described in the foregoing, the compound of the present invention has superior antiviral activity and permits provision of an antiviral agent efficacious for the preventive and therapeutic treatment of viral diseases caused typically by RS virus.

What is claimed is:

1. A pharmaceutical composition comprising an antiviral effective amount of a 1,4-dihydro-2,3-benzodithiin derivative of formula (I):

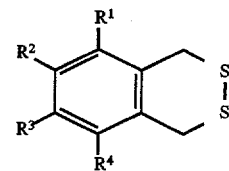

wherein $R^1$, $R^2$, $R^3$, and $R^4$ are each a hydrogen atom, an optionally substituted lower alkyl, an optionally substituted lower alkenyl, an optionally substituted aryl, an optionally substituted aralkyl, a nitro, a cyano, a carboxy, an alkoxycarbonyl, a lower alkylsulfinyl, an arylsulfinyl, a lower alkylsulfonyl, an arylsulfonyl, a sulfamoyl, a carbamoyl, an acyl, a hydrazino, a halogen atom, a group of the formula: $OR^5$, a group of the formula: $SR^5$ or a group of the formula: $NR^6R^7$ wherein $R^5$ is a hydrogen atom, an optionally substituted lower alkyl, an optionally substituted lower alkenyl, or an optionally substituted aryl, and $R^6$ and $R^7$ are each a hydrogen atom, an optionally substituted lower alkyl, an optionally substituted lower alkenyl, or an optionally substituted aryl, or a pharmacologically acceptable salt thereof and a pharmaceutically acceptable carrier.

2. A 1,4-dihydro-2,3-benzodithiin derivative of the formula (II)

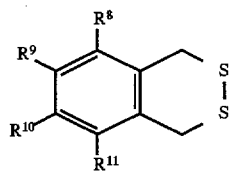
(II)
wherein $R^8$, $R^9$, $R^{10}$ and $R^{11}$ are each an optionally substituted lower alkyl or a halogen atom.
3. A method for treating viral diseases, which comprises administering to patients an antiviral effective amount of the pharmaceutical composition of claim 1.
* * * * *

UNITED STATES PATENT AND TRADEMARK OFFICE
CERTIFICATE OF CORRECTION

PATENT NO. : 5,698,580
DATED : December 16, 1997
INVENTOR(S) : Kajiyashiki et al.

It is certified that error appears in the above-identified patent and that said Letters Patent is hereby corrected as shown below:

ON THE TITLE PAGE:

References Cited: U.S. Patent Documents: "3,682,953" should read --3,682,963--.

IN THE SPECIFICATION:

In Column 1, line 33 "vital" should read --viral--.

In Column 2, line 50: "method" should read --methoxy--.

In Column 6, line 5: "mute" should read --route--.

Signed and Sealed this

Second Day of February, 1999

Attest:

Attesting Officer

Acting Commissioner of Patents and Trademarks